United States Patent [19]

Berg

[11] Patent Number: 4,786,370

[45] Date of Patent: Nov. 22, 1988

[54] DEHYDRATION OF FORMIC ACID BY EXTRACTIVE DISTILLATION

[76] Inventor: Lloyd Berg, 1314 S. Third Ave., Bozeman, Mont. 59715

[21] Appl. No.: 140,495

[22] Filed: Jan. 4, 1988

[51] Int. Cl.$^4$ .................... B01D 3/40; C07D 53/02
[52] U.S. Cl. ................................. 203/15; 203/51; 203/56; 203/58; 203/60; 203/61; 203/62; 203/65; 562/609
[58] Field of Search ............ 203/15, 16, 58, 51, 203/61, 60, 62, 57, 65, 56; 562/609

[56] References Cited

U.S. PATENT DOCUMENTS

| | | | |
|---|---|---|---|
| 2,437,519 | 3/1948 | Guinot et al. | 203/15 |
| 2,439,777 | 4/1948 | Lake et al. | 203/58 |
| 2,801,265 | 7/1957 | Coutor | 203/15 |
| 3,018,228 | 1/1962 | Cornell | 203/58 |
| 4,444,881 | 4/1984 | Urbas | 203/15 |
| 4,549,938 | 10/1985 | Berg et al. | 203/58 |
| 4,642,166 | 2/1987 | Berg et al. | 203/58 |
| 4,735,690 | 4/1988 | Berg et al. | 203/15 |

FOREIGN PATENT DOCUMENTS 234662  12/1963  Austria .................... 203/58

*Primary Examiner*—Wilbur Bascomb

[57] ABSTRACT

Formic acid cannot be completely removed from formic acid and water mixtures by distillation because of the presence of the maximum azeotrope. Formic acid can be readily removed from formic acid - water mixtures by extractive distillation in which the extractive agent is ethylene carbonate or propylene carbonate, either alone or mixed with certain high boiling organic compounds. Examples of effective agents are ethylene carbonate and heptanoic acid; propylene carbonate, benzoic acid and isophorone; propylene carbonate, heptanoic acid and 2-hydroxyacetophenone.

5 Claims, No Drawings

DEHYDRATION OF FORMIC ACID BY EXTRACTIVE DISTILLATION

FIELD OF THE INVENTION

This invention relates to a method for dehydrating formic acid using certain higher boilding liquids as the agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during the extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with lowest boiling component. This usually requires that the extractive agent boil twenty Centigrade degrees or more than the lowest boiling component.

At the bottom of a continuous column, the less volatile components of the close boiling mixtures and the extractive agent are continuously removed from the column. The usual methods of separation of these two components are the use of another rectification column, cooling and phase separation or solvent extraction.

There are currently two commercial methods for manufacturing formic acid. One is the reaction of caustic soda with carbon monoxide under pressure to produce sodium formate. This is then hydrolysed with sulfuric acid to yield the formic acid. The other is to obtain the formic acid as a by-product from the oxidation of n-butane. Both of these processes yield an aqueous mixture of formic acid. However the components of this mixture cannot be separated by conventional rectification because formic acid boils at 100.8° C., only 0.8° C. above water and because these two form a maximum azeotrope boiling at 107.2° C. and containing 22.5 wt.% water. Thus it is impossible to separate completely formic acid from water by rectification because of the closeness of the boiling points and because as soon as the maximum azeotrope composition is attained, no further change in composition will occur.

Extractive distillation would be an attractive method of effecting the separation of formic acid from water if agents can be found that (1) will break the formic acid-water azeotrope and (2) are easy to recover from formic acid, that is, form no azeotrope with formic acid and boil sufficiently above formic acid to make the separation by rectification possible with only a few theoretical plates.

Extractive distillation typically requires the addition of an equal amount to twice as much extractive agent as the formic acid-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is desirable that the extractive agent be miscible with formic acid otherwise it will form a two-phase azeotrope with the formic acid in the recovery column and some other method of separation will have to be employed. Recent attempts to separate formic acid from water were reported by Kokai, Japanese Pat. No. 82 24,324, Feb. 8, 1982 who used amines or phosphate esters to separate formic acid from water. Kawabata, Higuchi and Yoshida, J. Bull. Chem. Soc. Japan, 1981, 54(11), 3253-8 used poly(4-vinylpyridine) to remove the water from formic acid. Jahn, Est German Pat. No. 133,559, Jan. 10, 1979 separated acetic acid-formic acid-water mixtures in three successive columns and only got a partial dehydration of the formic acid. Berg & Yeh, U.S. Pat. No. 4,642,166 used sulfones to effect this separation by extractive distillation.

OBJECTIVE OF THE INVENTION

The object of this invention is to provide a process or method of extractive distillation that will enhance the relative volatility of water from formic acid in their separation in a rectification column. It is a further object of this invention to identify suitable extractive distillation agents which will eliminate the formic acid-water azeotrope and make possible the production of pure formic acid and water by rectification. It is a further object of this invention to identify organic compounds which are stable, can be separated from formic acid by rectification with relatively few plates and can be recycled to the extractive distillation column and reused with little decomposition.

SUMMARY OF THE INVENTION

The objects of the invention are provided by a process for separating formic acid from water which entails the use of certain organic compounds as the agent in extractive distillation.

TABLE 1

| Extractive Distillation Agents Containing Ethylene Carbonate | | | | |
|---|---|---|---|---|
| Compounds | Ratios | | Relative Volatility | |
| Ethylene carbonate (EtCb) | 1 | 6/5 | 2.2 | 2.5 |
| EtCb, Acetyl salicylic acid | $(\frac{1}{2})^2$ | $(3/5)^2$ | 1.8 | 1.4 |
| EtCb, Adipic acid | " | " | 1.6 | 1.7 |
| EtCb, Azelaic acid | " | " | 1.7 | 1.9 |
| EtCb, Benzoic acid | " | " | 2.7 | 2.6 |
| EtCb, Benzyl benzoate | " | " | 1.5 | 2.1 |
| EtCb, Cinnamic acid | " | " | 1.7 | 1.7 |
| EtCb, Glutaric acid | " | " | 2.2 | 1.8 |

TABLE 1-continued

Extractive Distillation Agents Containing Ethylene Carbonate

| Compounds | Ratios | | Relative Volatility | |
|---|---|---|---|---|
| EtCb, Heptanoic acid | " | " | 2.1 | 2.3 |
| EtCb, Hexanoic acid | " | " | 2.2 | 2.5 |
| EtCb, Isophorone | " | " | 2.5 | 3.2 |
| EtCb, Itaconic acid | " | " | 2.1 | 2.0 |
| EtCb, Malic acid | " | " | 1.4 | 1.7 |
| EtCb, Octanoic acid | " | " | 2.3 | 2.2 |
| EtCb, Pelargonic acid | " | " | 2.1 | 2.2 |
| EtCb, Salicylic acid | " | " | 2.4 | 2.6 |
| EtCb, Sebacic acid | " | " | 1.7 | 1.4 |
| EtCb, o-Toluic acid | " | " | 2.0 | 2.6 |
| EtCb, m-Toluic acid | " | " | 2.1 | 2.0 |
| EtCb, Acetyl salicylic acid, Isophorone | $(\frac{1}{2})^3$ | $(2/5)^3$ | 2.2 | 2.2 |
| EtCb, Adipic acid, Ethyl benzoate | " | " | 1.6 | 1.3 |
| EtCb, Azelaic acid, Acetophenone | " | " | 2.5 | 2.6 |
| EtCb, Benzoic acid, 2-Hydroxy-acetophenone | " | " | 2.6 | 2.5 |
| EtCb, p-Tert. Butyl benzoic acid, Benzyl benzoate | " | " | 1.5 | 1.4 |
| EtCb, Cinnamic acid, Cyclohexanone | " | " | 2.1 | 1.8 |
| EtCb, Dodecanedioic acid, Benzyl benzoate | " | " | 1.7 | 2.3 |
| EtCb, Glutaric acid, Diethylene glycol dibenzoate | " | " | 1.7 | 2.0 |
| EtCb, Heptanoic acid, Acetyl salicylic acid | " | " | 2.1 | 2.1 |
| EtCb, Heptanoic acid, 2-Hydroxy-acetophenone | " | " | 2.1 | 2.5 |
| EtCb, Heptanoic acid, Isophorone | " | " | 2.3 | 2.6 |
| EtCb, Hexanoic acid, Acetophenone | " | " | 2.6 | 3.0 |
| EtCb, Hexanoic acid, Benzoic acid | " | " | 1.7 | 2.2 |
| EtCb, Hexanoic acid, Isophorone | " | " | 2.4 | 2.6 |
| EtCb, Itaconic acid, Methyl salicylate | " | " | 1.7 | 2.6 |
| EtCb, Malic acid, Methyl isoamyl ketone | " | " | 1.8 | 1.8 |
| EtCb, Neodecanoic acid, Isophorone | " | " | 2.2 | 2.2 |
| EtCb, Octanoic acid, Benzoic acid | " | " | 1.8 | 2.4 |
| EtCb, Octanoic acid, Isophorone | " | " | 2.7 | 3.4 |
| EtCb, Pelargonic acid, Cyclohexanone | $(\frac{1}{2})^3$ | $(2/5)^3$ | 2.3 | 2.2 |
| EtCb, Pelargonic acid, Isophorone | " | " | 2.8 | 2.9 |
| EtCb, Salicylic acid, Isophorone | " | " | 2.2 | 2.6 |
| EtCb, Sebacic acid, Methyl n-amyl ketone | " | " | 1.8 | 2.2 |
| EtCb, o-Toluic acid, Benzonitrile | " | " | 2.5 | 2.8 |
| EtCb, m-Toluic acid, 2,4-Pentanedione | " | " | 2.7 | 2.7 |
| EtCb, p-Toluic acid, 2,4-Pentanedione | " | " | 2.2 | 1.8 |

TABLE 2

Extractive Distillation Agents Containing Propylene Carbonate

| Compounds | Ratios | | Relative Volatility | |
|---|---|---|---|---|
| Propylene carbonate (PrCb) | 1 | 6/5 | 2.0 | 2.4 |

TABLE 2-continued

Extractive Distillation Agents Containing Propylene Carbonate

| Compounds | Ratios | | Relative Volatility | |
|---|---|---|---|---|
| PrCb, Acetyl salicylic acid | $(\frac{1}{2})^2$ | $(3/5)^2$ | 1.7 | 2.1 |
| PrCb, Adipic acid | " | " | 1.9 | 1.6 |
| PrCb, Benzoic acid | " | " | 2.6 | 2.4 |
| PrCb, Butyl benzoate | " | " | 1.8 | 2.0 |
| PrCb, Cinnamic acid | " | " | 1.7 | 1.9 |
| PrCb, Decanoic acid | " | " | 1.8 | 2.0 |
| PrCb, Heptanoic acid | " | " | 2.0 | 2.3 |
| PrCb, Hexanoic acid | " | " | 1.9 | 1.9 |
| PrCb, 2-Hydroxyacetophenone | " | " | 1.5 | 1.7 |
| PrCb, Isophorone | " | " | 2.4 | 2.3 |
| PrCb, Octanoic acid | " | " | 1.9 | 2.2 |
| PrCb, Pelargonic acid | " | " | 1.7 | 2.2 |
| PrCb, Salicylic acid | " | " | 2.1 | 2.1 |
| PrCb, Sebacic acid | " | " | 2.0 | 1.4 |
| PrCb, o-Toluic acid | " | " | 1.6 | 2.2 |
| PrCb, m-Toluic acid | " | " | 2.5 | 2.3 |
| PrCb, Malic acid | " | " | 1.9 | 1.4 |
| PrCb, Acetyl salicylic acid, 2-Hydroxy-acetophenone | $(\frac{1}{3})^3$ | $(2/5)^3$ | 1.7 | 2.0 |
| PrCb, Benzoic acid, Isophorone | " | " | 2.9 | 2.9 |
| PrCb, Cinnamic acid, Isophorone | " | " | 2.4 | 2.1 |
| PrCb, Decanoic acid, 4-Methyl-2-pentanone | " | " | 1.7 | 2.0 |
| PrCb, Dodecanedoic acid, Butyl benzoate | " | " | 1.8 | 1.8 |
| PrCb, Heptanoic acid, Isophorone | " | " | 2.4 | 2.1 |
| PrCb, Heptanoic acid, 4-Methyl-2-pentanone | " | " | 2.5 | 2.7 |
| PrCb, Hexanoic acid, Acetophenone | " | " | 1.9 | 2.0 |
| PrCb, Hexanoic acid, Isophorone | " | " | 1.9 | 2.1 |
| PrCb, Malic acid, Ethyl butyl ketone | " | " | 2.0 | 1.5 |
| PrCb, Neodecanoic acid, Cyclohexanone | " | " | 1.8 | 1.8 |
| PrCb, Octanoic acid, Acetophenone | " | " | 1.9 | 2.2 |
| PrCb, Pelargonic acid, 2-Hydroxyacetophenone | $(\frac{1}{3})^3$ | $(2/5)^3$ | 2.1 | 2.5 |
| PrCb, Pelargonic acid, Isophorone | " | " | 2.6 | 2.7 |
| PrCb, Pelargonic acid, 4-Methyl-2-pentanone | " | " | 1.8 | 1.9 |
| PrCb, Salicylic acid, Isophorone | " | " | 2.3 | 2.6 |
| PrCb, Sebacic acid, Benzyl benzoate | " | " | 1.4 | 1.4 |
| PrCb, o-Toluic acid, Dipropylene glycol dibenzoate | " | " | 1.8 | 2.1 |
| PrCb, m-Toluic acid, Benzophenone | " | " | 2.8 | 2.8 |
| PrCb, p-Toluic acid, Isophorone | " | " | 2.2 | 1.9 |

TABLE 3

Data From Runs Made In Rectification Column

| Agent | Column | Time, Hrs. | Weight % Water | Weight % Formic acid | Relative Volatility |
|---|---|---|---|---|---|
| 33% Propylene carbonate, | Overhead | 1 | 96.9 | 3.1 | |
| 33% Heptanoic acid | Bottoms | | 56.5 | 43.5 | 2.06 |
| 33% 2-Hydroxyacetophenone | Overhead | 2 | 97.5 | 2.5 | |
| | Bottoms | | 55.3 | 44.7 | 2.14 |
| | Overhead | 3 | 97.9 | 2.1 | |
| | Bottoms | | 51.5 | 46.5 | 2.30 |
| 50% Propylene carbonate | Overhead | 0.5 | 93.8 | 6.2 | |
| 25% Benzoic acid | Bottoms | | 58.6 | 41.4 | 1.70 |
| 25% Isophorone | Overhead | 1 | 98.1 | 1.9 | |
| | Bottoms | | 53.2 | 46.8 | 2.35 |
| | Overhead | 2 | 98.5 | 1.5 | |
| | Bottoms | | 56.1 | 43.9 | 2.40 |
| 50% Ethylene carbonate | Overhead | 1 | 97.5 | 2.5 | |
| 50% Heptanoic acid | Bottoms | | 58.6 | 41.4 | 2.08 |
| | Overhead | 2 | 98.9 | 1.1 | |
| | Bottoms | | 57.0 | 43.0 | 2.56 |
| | Overhead | 2.5 | 99.1 | 0.9 | |
| | | | 60.9 | 39.1 | 2.60 |

DETAILED DESCRIPTION OF THE INVENTION

We have discovered that ethylene carbonate and propylene carbonate, either alone or admixed with other high boiling organic compounds, will effectively negate the formic acid-water maximum azeotrope and permit the separation of water from formic acid by rectification when employed as the agent in extractive distillation. Table 1 lists ethylene carbonate and its mixtures and the approximate proportions that we have found to be effective. Table 2 lists propylene carbonate and its mixtures. The data in Tables 1 and 2 was obtained in a vapor-liquid equilibrium still. In each case, the starting material was the formic acid-water azeotrope. The ratios are the parts by weight of extractive agent used per part of formic acid-water azeotrope. The relative volatilities are listed for each of the two ratios employed. The compounds which are effective when used in mixtures with ethylene carbonate are acetyl salicylic acid, adipic acid, azelaic acid, benzoic acid, benzyl benzoate, cinnamic acid, glutaric acid, heptanoic acid, hexanoic acid, isophorone, itaconic acid, malic acid, octanoic acid, pelargonic acid, salicyclic acid, sebacic acid, o-toluic acid, m-toluic acid, p-toluic acid, ethyl benzoate, acetophenone, 2-hyroxyacetophenone, p-tertiary butyl benzoic acid, cyclohexanone, dodecanedioic acid, glutaric acid, diethylene glycol dibenzoate, methyl salicylate, methyl isoamyl ketone, neodecanoic acid, methyl n-amyl ketone, benzonitrile and 2,4-pentanedione. The compounds which are effective when used in mixtures with propylene carbonate are acetyl salicylic acid, adipic acid, benzoic acid, butyl benzoate, cinnamic acid, decanoic acid, heptanoic acid, hexanoic acid, 2-hydroxyacetophenone, isophorone, octanoic acid, pelargonic acid, salicylic acid, sebacic acid, o-toluic acid, m-toluic acid, p-toluic acid, malic acid, 4-methyl-2-pentanone, dodecanedioic acid, acetophenone, ethyl butyl ketone, neodecanoic acid, cyclohexanone, benzyl benzoate, dipropylene glycol dibenzoate and benzophenone.

The two relative volatilities shown in Tables 1 and 2 correspond to the two different ratios investigated. For example, in Table 1, one part of ethylene carbonate mixed with one part of the formic acid-water azeotrope gives a relative volatility of 2.2; with 6/5 parts of ethylene carbonate, the relative volatility is 2.5. One half part of ethylene carbonate mixed with one half part of isophorone with one part of the formic acid-water azeotrope gives a relative volatility of 2.5; 3/5 parts of ethylene carbonate plus 3/5 parts of isophorone give 3.2. One third part of ethylene carbonate plus ⅓ part of hexanoic acid plus ⅓ part of acetophenone with one part of the formic acid-water azeotrope gives a relative volatility of 2.6; with 2/5 parts, these three give a relative volatility of 3.0. In every example in Tables 1 and 2, the starting material is the formic acid-water azeotrope which possesses a relative volatility of 1.00.

One of the mixtures, propylene carbonate, benzoic acid and isophorone, listed in Table 2 and whose relative volatility had been determined in the vapor-liquid equilibrium still, was then evaluated in a glass perforated plate rectification column possessing 4.5 theoretical plates and the results listed in Table 3. The data in Table 3 was obtained in the following manner. The charge was 85 wt.% formic acid and 15% water and after a half hour of operation in the 4.5 theoretical plate column to establish equilibrium, 50% propylene carbonate, 25% benzoic acid and 25% isophorone at 95° C. and 20 ml/min. was pumped in. The rectification was continued with sampling of overhead and bottoms after ½ hour. The analysis is shown in Table 3 and was 93.8% water, 6.2% formic acid in the overhead and 58.6% water, 41.4% formic acid in the bottoms which gives a relative volatility of 1.20 of water to formic acid. After one hour of continuous operation, the overhead was 98.1% water, 1.9% formic acid, the bottoms was 53.2% water, 46.8% formic acid which is a relative volatility of 2.35. After two hours of continuous operation, the overhead was 98.5% water, 1.5% formic acid, the bottoms was 56.1% water, 43.9% formic acid which is a relative volatility of 2.40. This indicates that the maximum azeotrope has been negated and separation accomplished. Without the extractive agent, the overhead would have approached the maximum azeotrope composition of 22.5% water. This proves that the extractive agent is negating the azeotrope and makes the rectification proceed as if the azeotrope no longer existed and brings out the more volatile component, water, as overhead. And this from formic acid which normally boils only 0.8° C. higher.

THE USEFULNESS OF THE INVENTION

The usefulness or utility of this invention can be demonstrated by referring to the data presented in Tables, 2 and 3. All of the successful extractive distillation agents show that formic acid and water can be separated from their maximum azeotrope by means of distillation in a rectification column and that the ease of separation as measured by relative volatility is considerable. Without these extractive distillation agents, no improvement above the azeotrope composition will occur in the rectification column. The data also show that the most attractive agents will operate at a boilup rate low enough to make this a useful and efficient method of recovering high purity formic acid from any mixture with water including the maximum azeotrope. The stability of the compounds used and the boiling point difference is such that complete recovery and recycle is obtainable by a simple distillation and the amount required for make-up is small.

WORKING EXAMPLES

Example 1

Fifty grams of the formic acid-water azeotrope, 25 grams of ethylene carbonate and 25 grams of glutaric acid were charged to the vapor-liquid equilibrium still and refluxed for 15 hours. Analysis indicated a vapor composition of 68.9% water, 31.1% formic acid, a liquid composition of 50% water, 50% formic acid which is a relative volatility of 2.2. Five grams of ethylene carbonate and five grams of glutaric acid were added and refluxing continued for another eight hours. Analysis indicated a vapor composition of of 72.4% water, 27.6% formic acid, a liquid composition of 48.1% water, 51.9% formic acid which is a relative volatility of 2.8.

Example 2

Fifty grams of the formic acid-water azeotrope, 17 grams of propylene carbonate, 17 grams of m-toluic acid and 17 grams of benzophenone were charged to the vapor-liquid equilibrium still and refluxed for 13 hours. Analysis indicated a vapor composition of 69.6% water, 30.4% formic acid, a liquid composition of 45% water, 55% formic acid which is a relative volatility of 2.8. Three grams each of propylene carbonate, m-toluic caid and benzophenone were added and refluxing continued for another eleven hours. Analysis indicated a vapor composition of 70.1% water, 29.9% formic acid, a liquid composition of 44.7% water, 55.3% formic acid which is a relative volatility of 2.8.

Example 3

A glass perforated plate rectification column was calibrated with ethylbenzene and p-xylene which possesses a relative volatility of 1.06 and found to have 4.5 theoretical plates. A solution comprising 340 grams of formic acid and 60 grams of water was placed in the stillpot and heated. When refluxing began, an extractive agent comprising 33% propylene carbonate, 33% heptanoic acid and 33% 2-hydroxyacetophenone was pumped into the column at a rate of 20 ml/min. The temperature of the extractive agent as it entered the column was 95° C. After establishing the feed rate of the extractive agent, the heat input to the formic acid and water in the stillpot was adjusted to give a total reflux rate of 10–20 ml/min. After one hour of operation, the overhead and bottoms samples of approximately two ml. were collected and analysed by gas chromatography. The overhead analysis was 96.9% water, 3.1% formic acid. The bottoms analysis was 56.5% water, 43.5% formic acid. Using these compositions in the Fenske equation, with the number of theoretical plates in the column being 4.5, gave an average relative volatility of 2.06 for each theoretical plate. After two hours of total operating time, the overhead and bottoms samples were again taken and analysed. The overhead composition was 97.5% water, 2.5% formic acid and the bottoms composition was 55.3% water, 44.7% formic acid. This gave an average relative volatility 2.14 for each theoretical plate. After three hours of total opearting time, the overhead and bottoms samples were again taken and analysed. The overhead composition was 97.9% water, 2.1% formic acid and the bottoms composition was 51.5% water, 46.5% formic acid. This gave an average relative volatility of 2.30 for each theoretical plate.

Example 4

Using the same column as in Example 3, an extractive agent consisting of 50% propylene carbonate, 25% benzoic acid and 25% isophorone was pumped into the column at a rate of 20 ml/min. After one-half hour of operation, the overhead analysis was 93.8% water, 6.2% formic acid, the bottoms composition was 58.6% water, 41.4% formic acid which is an average relative volatility of 1.70. After one hour of total operating time, the overhead composition was 98.1% water, 1.9% formic acid, the bottoms composition was 53.2% water, 46.8% formic acid which is an average relative volatility of 2.35 for each theoretical plate. After two hours of total operating time, the overhead composition was 98.5% water, 1.5% formic acid, the bottoms composition was 56.1% water, 43.9% formic acid which is an average relative volatility of 2.40 for each theoretical plate.

Example 5

Using the same column as in Example 3, an extractive agent consisting of 50% ethylene carbonate and 50% heptanoic acid was pumped into the column at a rate of 20 ml/min. After one hour of operation, the overhead analysis was 97.5% water, 2.5% formic acid, the bottoms composition was 58.6% water, 41.4% which is an average relative volatility of 2.08. After two hours of total operating time, the overhead composition was 98.9% water, 1.1% formic acid, the bottoms composition was 57% water, 43% formic acid which is an average relative volatility of 2.56 for each theoretical plate. After 2.5 hours of total operating time, the overhead composition was 99.1% water, 0.9% formic acid, the bottoms composition was 60.9% water, 39.1% formic acid which is an average relative volatility of 2.60 for each theoretical plate. The data for Examples 3, 4 and 5 is listed in Table 3.

We claim:

1. A method for recovering formic acid from mixtures of formic acid and water which comprises distilling a mixture of formic acid and water in a rectification column in the presence of about one part of an extractive agent per part of formic acid-water mixture, recovering water as overhead product and obtaining the formic acid and the extractive agent from the stillpot, wherein said extractive agent is a material selected from the group consisting of propylene carbonate and ethylene carbonate.

2. The method of claim 1 in which the extractive agent comprises ethylene carbonate.

3. The method of claim 1 in which the extractive agent comprises propylene carbonate.

4. The method of claim 1 in which the extractive agent comprises ethylene carbonate and at least one member from the group consisting of acetyl salicylic acid, adipic acid, azelaic acid, benzoic acid, benzyl benzoate, cinnamic acid, glutaric acid, heptanoic acid, hexanoic acid, isophorone, itaconic acid, malic acid, octanoic acid, pelargonic acid, salicylic acid, sebacic acid, o-toluic acid, m-toluic acid, p-toluic acid, ethyl benzoate, acetophenone, 2-hydroxyacetophenone, p-tertiary butyl benzoic acid, cyclohexanone, dodecanedioic acid, glutaric acid, diethylene glycol dibenzoate, methyl salicylate, methyl n-amyl ketone, benzonitrile and 2,4-pentanedione.

5. The method of claim 1 in which the extractive agent comprises propylene carbonate and at least one member from the group consisting of acetyl salicylic acid, adipic acid, benzoic acid, butyl benzoate, cinnamic acid, decanoic acid, heptanoic acid, hexanoic acid, isophorone, 2-hydroxyacetophenone, octanoic acid, pelargonic acid, salicylic acid, sebacic acid, o-toluic acid, m-toluic acid, p-toluic acid, malic acid, 4-methyl-2-pentanone, dodecanedioic acid, acetophenone, ethyl butyl ketone, neodecanoic acid, cyclohexanone, benzyl benzoate, benzophenone and dipropylene glycol dibenzoate.

* * * * *